United States Patent
Negi et al.

(10) Patent No.: US 10,172,558 B2
(45) Date of Patent: Jan. 8, 2019

(54) STRUCTURE AND METHODOLOGY FOR A SHADOW MASK HAVING HOLLOW HIGH ASPECT RATIO PROJECTIONS

(71) Applicant: University of Utah Research Foundation, Salt Lake City, UT (US)

(72) Inventors: Sandeep Negi, Salt Lake City, UT (US); Rajmohan Bhandari, Salt Lake City, UT (US); Mobashir Hasan Shandi, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 58 days.

(21) Appl. No.: 15/261,648

(22) Filed: Sep. 9, 2016

(65) Prior Publication Data

US 2017/0071540 A1    Mar. 16, 2017

Related U.S. Application Data

(60) Provisional application No. 62/216,908, filed on Sep. 10, 2015, provisional application No. 62/358,258, filed on Jul. 5, 2016.

(51) Int. Cl.
*A61B 5/00* (2006.01)
*B81B 1/00* (2006.01)
(Continued)

(52) U.S. Cl.
CPC .......... *A61B 5/685* (2013.01); *A61B 5/04001* (2013.01); *A61N 1/05* (2013.01);
(Continued)

(58) Field of Classification Search
CPC ...................................................... A61B 5/685
See application file for complete search history.

(56) References Cited

U.S. PATENT DOCUMENTS 4,452,249 A * 6/1984 Sachs ..................... A61N 1/044
204/403.01
5,017,513 A * 5/1991 Takeuchi ............ H01L 21/3081
257/E21.232
(Continued)

FOREIGN PATENT DOCUMENTS

| WO | WO 2014/105458 | 7/2014 |
| WO | WO 2014/127309 | 8/2014 |
| WO | WO 2015/143443 | 9/2015 |

OTHER PUBLICATIONS

Kim et al., Fabrication of High-Aspect-Ratio Nano Structures Using a Nano X-ray Shadow Mask, J. Micromech. Microeng. 18, Nov. 28, 2007, 1-7.
(Continued)

*Primary Examiner* — Benjamin Sandvik
(74) *Attorney, Agent, or Firm* — Thrope North & Western, LLP

(57) ABSTRACT

A high aspect ratio shadow mask and a method of making and using the high aspect ratio shadow mask can provide multiple conductive trace pathways along high aspect ratio electrodes. The high aspect ratio shadow mask can include a substantially planar base layer and a plurality of hollow high aspect ratio projections extending from the substantially planar base layer. The high aspect ratio shadow mask can further include a plurality of openings along the hollow projections which define trace deposition patterns.

22 Claims, 5 Drawing Sheets

(51) Int. Cl.
*B81C 1/00* (2006.01)
*A61B 5/04* (2006.01)
*A61N 1/05* (2006.01)
*C25D 5/34* (2006.01)
*C25D 1/00* (2006.01)
*C25D 1/08* (2006.01)

(52) U.S. Cl.
CPC ............ *A61N 1/0502* (2013.01); *B81B 1/008* (2013.01); *B81C 1/00111* (2013.01); *C25D 1/003* (2013.01); *C25D 1/08* (2013.01); *C25D 5/34* (2013.01); *A61B 2562/0209* (2013.01); *A61B 2562/046* (2013.01); *A61B 2562/125* (2013.01); *B81B 2201/055* (2013.01)

(56) References Cited

U.S. PATENT DOCUMENTS

| | | | | |
|---|---|---|---|---|
| 5,215,088 | A * | 6/1993 | Normann | A61B 5/04001 600/377 |
| 6,558,361 | B1 * | 5/2003 | Yeshurun | A61M 37/0015 604/272 |
| 7,991,475 | B1 * | 8/2011 | Tang | A61B 5/04001 600/373 |
| 8,131,375 | B2 * | 3/2012 | Greenberg | A61F 9/08 607/54 |
| 8,232,074 | B2 * | 7/2012 | Jardemark | B82Y 15/00 204/451 |
| 9,669,209 | B2 * | 6/2017 | Neysmith | H05K 3/4644 |
| 9,719,163 | B2 * | 8/2017 | Han | C23C 14/042 |
| 9,737,247 | B2 * | 8/2017 | Wang | A61M 5/158 |
| 9,743,870 | B2 * | 8/2017 | Wang | A61B 5/1473 |
| 2002/0106496 | A1 * | 8/2002 | Moxon | A61B 5/04001 428/210 |
| 2002/0188310 | A1 | 12/2002 | Seward et al. | |
| 2003/0100823 | A1 * | 5/2003 | Kipke | A61B 5/04001 600/378 |
| 2004/0063100 | A1 * | 4/2004 | Wang | B81B 1/008 435/6.11 |
| 2004/0126707 | A1 | 7/2004 | Liu et al. | |
| 2005/0121411 | A1 | 6/2005 | Cohen | |
| 2006/0276866 | A1 * | 12/2006 | McCreery | A61N 1/0534 607/116 |
| 2008/0138581 | A1 * | 6/2008 | Bhandari | G03F 7/16 428/156 |
| 2008/0138582 | A1 | 6/2008 | Bhandari et al. | |
| 2008/0157427 | A1 | 7/2008 | Chiou et al. | |
| 2009/0035525 | A1 | 2/2009 | Garcia et al. | |
| 2009/0299167 | A1 * | 12/2009 | Seymour | A61B 5/04001 600/393 |
| 2009/0301994 | A1 | 12/2009 | Bhandari et al. | |
| 2010/0006536 | A1 | 1/2010 | Kalvesten et al. | |
| 2010/0062142 | A1 | 3/2010 | Zhu et al. | |
| 2010/0280457 | A1 | 11/2010 | Tokumoto et al. | |
| 2010/0305516 | A1 * | 12/2010 | Xu | A61M 37/0015 604/272 |
| 2011/0005669 | A1 * | 1/2011 | Lee | A61B 5/685 156/256 |
| 2011/0106229 | A1 * | 5/2011 | Ortmann | A61B 5/04001 607/116 |
| 2011/0237921 | A1 * | 9/2011 | Askin | A61B 5/0408 600/377 |
| 2012/0319705 | A1 * | 12/2012 | Schober | A61B 5/685 324/658 |
| 2013/0072808 | A1 * | 3/2013 | Neves | A61B 5/685 600/544 |
| 2013/0090542 | A1 * | 4/2013 | Kipke | A61B 5/04001 600/377 |
| 2013/0190851 | A1 * | 7/2013 | Schouenborg | A61N 1/0536 607/116 |
| 2013/0306356 | A1 | 11/2013 | Allen et al. | |
| 2014/0011013 | A1 | 1/2014 | Jin et al. | |
| 2014/0107446 | A1 * | 4/2014 | Tolosa | A61B 5/04001 600/345 |
| 2015/0080802 | A1 | 3/2015 | Kang et al. | |
| 2016/0066789 | A1 * | 3/2016 | Rogers | A61N 1/05 604/20 |
| 2016/0220135 | A1 * | 8/2016 | Negi | A61B 5/685 |
| 2017/0007813 | A1 * | 1/2017 | Negi | A61M 37/0015 |

OTHER PUBLICATIONS

Parker et al., Bulk Titanium Microneedles with Embedded Microfluidic Networks for Transdermal Drug Delivery, www.ieee.org, http://ieeexplore.ieee.org/document/1627845/, May 8, 2006, 4 pages, IEEE.

Yoon et al., A Novel Microneedle-Based Non-Enzymatic Glucose Sensor for Painless Diabetes Testing Application, Solid-State Sensors, Actuators and Mocrosystems Conference, Transducers, Aug. 1, 2011, 2164-2167, IEEE.

Selvarasah et al.; A Reusable High Aspect Ratio Parylene-C Shadow Mask Technology for Diverse Micropatterning Applications; Sensors and Actuators A 145-146, Oct. 26, 2007, 306-315, Elsevier.

Wise et al.; Wireless Implantable Microsystems: High-density Electronic Interfaces to the Nervous System; Proceedings of the IEEE, vol. 92. No. 1 Jan. 2004, 76-97.

* cited by examiner

STRUCTURE AND METHODOLOGY FOR A SHADOW MASK HAVING HOLLOW HIGH ASPECT RATIO PROJECTIONS

RELATED APPLICATIONS

This application claims priority to U.S. Provisional Application No. 62/216,908 filed on Sep. 10, 2015, and U.S. Provisional Application No. 62/358,258 filed on Jul. 5, 2016, which is herein incorporated by reference.

GOVERNMENT INTEREST

This invention was made with government support under R01 NS085213 awarded by the National Institutes of Health. The government has certain rights in the invention.

BACKGROUND

Microelectrode arrays contain multiple projections with an electrode through which neural signals can be measured, monitored, and/or stimulated. Electrodes on the array change the voltage environment around the neurons and can induce or receive an electric current from surrounding bioelectrical activity. The proximity of the electrode to neurons dictates the strength of signals and ultimately the number of signals that actually reach neurons which affects the overall efficacy of the microelectrode array.

Given the small scale of microelectrode arrays, manufacturing difficulties have limited the number of electrodes that can be placed on each projection. In the case of three-dimensional Utah microelectrode arrays a single electrode is oriented at the tip of each projection in the array. These electrodes are electrically isolated from one another and serve as independent electrodes. The placement of the electrodes at the tip of each projection measures, monitors, and/or stimulates neurons proximate the tip of the projection.

SUMMARY

Neurons that are located along adjacent sides of the electrodes projections may not be detected or may not receive a signal from the electrode. Therefore, the ability to make and use a three-dimensional microelectrode array with multiple electrodes oriented at various locations across the electrode would be an advancement in the art.

Accordingly, a high aspect ratio shadow mask is presented which can facilitate manufacture of such electrodes. The high aspect ratio shadow mask can include a substantially planar base layer and a plurality of hollow high aspect ratio projections extending from the substantially planar base layer. The high aspect ratio shadow mask can further include a plurality of openings along the hollow projections which define trace deposition patterns. In one example, the high aspect ratio projections can be arranged perpendicular to the substantially planar base layer, although angled or non-perpendicular projections may also be formed with respect to the base.

In another embodiment, a method of making a high aspect ratio shadow mask is presented. The method can include (1) acquiring a high aspect ratio array structure, (2) conformally depositing or placing a shadow mask layer of material on top of the high aspect ratio electrode array structure, and (3) removing the high aspect ratio structure from the shadow mask layer. The shadow mask layer can include a plurality of openings which can be formed along high aspect ratio features within the structure to define trace deposition patterns. Typically, the openings can be slits corresponding to the trace patterns, although other feature patterns such as contact pads, interdigitated electrodes (IDE), electrodes, and the like can also be formed. In some examples, the step of removing the high aspect ratio structure from the shadow mask layer can include dissolving or detaching the high aspect ratio structure.

In a further embodiment, a method of using a high aspect ratio shadow mask to create an electrode pattern on a high aspect ratio microelectrode array is presented. The method can include (1) acquiring a high aspect ratio shadow mask, (2) acquiring a high aspect ratio array structure, (3) aligning the high aspect ratio shadow mask over the high aspect ratio array structure, (4) depositing trace deposition materials over the high aspect ratio shadow mask, and (5) removing the high aspect ratio shadow mask to yield a microelectrode array structure comprising the electrode pattern. Removal and reuse of the shadow mask can benefit from alignment of the projections parallel to one another. However, non-parallel projections (with respect to one another) and/or non-perpendicular projections (with respect to the base layer) can be used when, for example, the shadow mask is sufficiently flexible and resilient to allow removal of the mask, or when the shadow mask can be destroyed upon removal. During the depositing step, trace deposition materials can penetrate through the plurality of openings along the hollow projections to form an electrode pattern on the microelectrode array structure.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1:
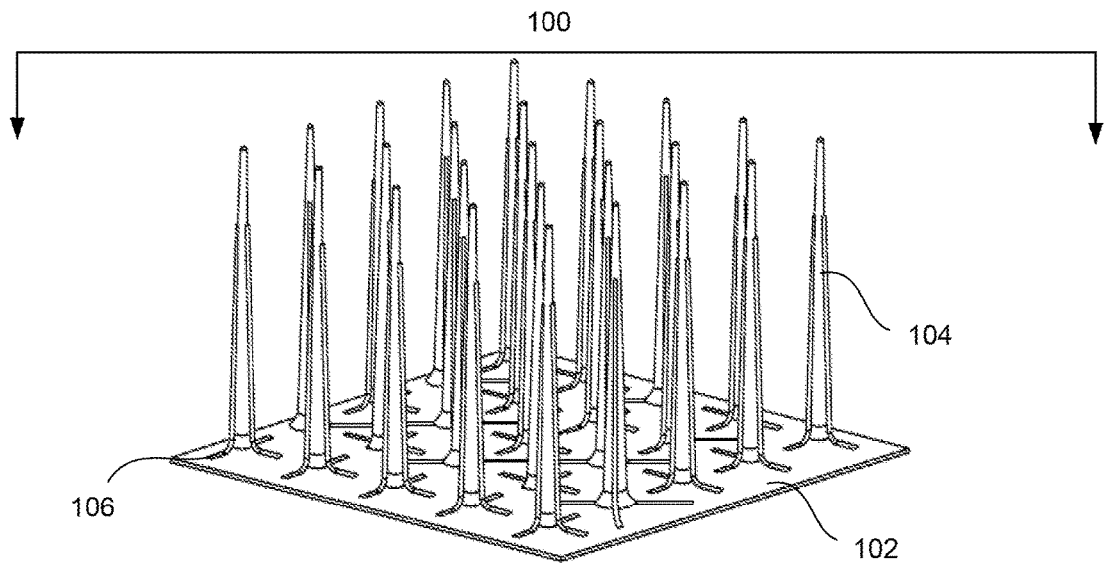
FIG. 1 is a high aspect ratio shadow mask in accordance with one example.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

It is noted that, as used in this specification and in the appended claims, the singular forms "a," "an," and "the" include plural referents unless the context clearly dictates otherwise. Thus, for example, reference to "a layer" includes one or more of such features, reference to "an opening" includes reference to one or more of such elements, and reference to "processing" includes reference to one or more of such steps.

As used herein, the terms "about" and "approximately" are used to provide flexibility, such as to indicate, for example, that a given value in a numerical range endpoint may be "a little above" or "a little below" the endpoint. The degree of flexibility for a particular variable can be readily determined by one skilled in the art based on the context.

As used herein, the term "substantially" refers to the complete or nearly complete extent or degree of an action, characteristic, property, state, structure, item, or result. The exact allowable degree of deviation from absolute completeness may in some cases depend on the specific context. However, the nearness of completion will generally be so as to have the same overall result as if absolute and total completion were obtained. The use of "substantially" is equally applicable when used in a negative connotation to refer to the complete or near complete lack of an action, characteristic, property, state, structure, item, or result.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Reference will now be made to the exemplary embodiments illustrated, and specific language will be used herein to describe the same. It will nevertheless be understood that no limitation of the scope of the technology is thereby intended. Additional features and advantages of the technology will be apparent from the detailed description which follows, taken in conjunction with the accompanying drawings, which together illustrate, by way of example, features of the technology.

Presented herein is a high aspect ratio shadow mask. In one example shown in FIG. 1, the high aspect ratio shadow mask 100 can include a substantially planar base layer 102, a plurality of hollow high aspect ratio projections 104 arranged perpendicular to the substantially planar base layer 102, and a plurality of openings 106 along the hollow projections 104 that can define trace deposition patterns. In some examples, the hollow high aspect ratio projections can extend at an angle other than a right angle, such that the projections are not perpendicular to the substantially planer base.

Figure 2:
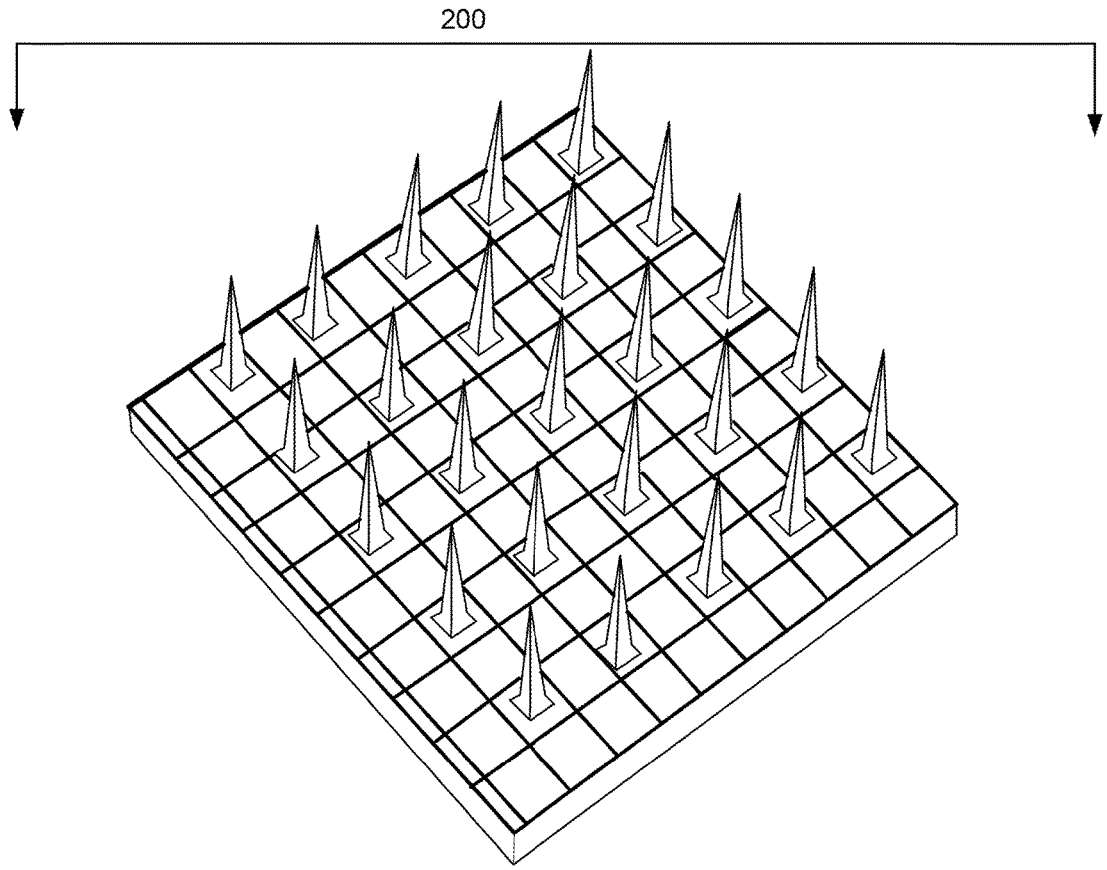
FIG. 2 is a high aspect ratio microneedle array in accordance with an UEA as described herein upon which the shadow mask of FIG. 1 may be placed in accordance with one example.

The high aspect ratio shadow mask is a stencil or mask device designed to be placed or otherwise formed over a high aspect ratio microneedle array (MEA) 200, such as shown in FIG. 2, and can be used to guide deposition of conductive traces such as a metal along the sides of the microneedles on the MEA. The high aspect shadow mask can be used in conjunction with any MEA array. In one example, the MEA can be a micro-wire, silicon based, or a flexible MEA. In another example, the microneedle array (MEA) can be a Utah electrode array (UEA). In another example, the MEA can be a flexible polyimide based MEA. Other non-limiting examples of MEA can include planar and non-planar configurations, and the like.

The MEA that the high aspect ratio is used in connection with can also vary. In one example, the MEA's can be a standard 4×4, 5×5, 6×6, 8×8, 10×10, 12×12, array or a combination of any of these electrode array structures. In another example, the MEA can be a high definition array having hundreds to thousands of individual arrays. In yet another example, the MEA can be a 6×5 array. In a further example, the MEA can be a CMOS high-density MEA. In one example, such an MEA can have an aspect ratio of from 8:1 to 30:1, such as about 15:1.

Figure 3:
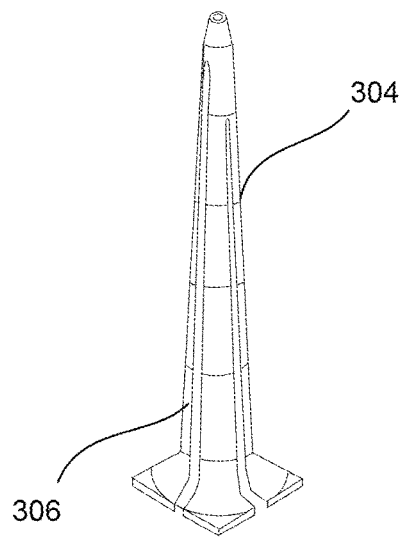
FIG. 3 is a close up view of one hollow high aspect ratio projection in a high aspect ratio shadow mask in accordance with one example.
Figure 4:
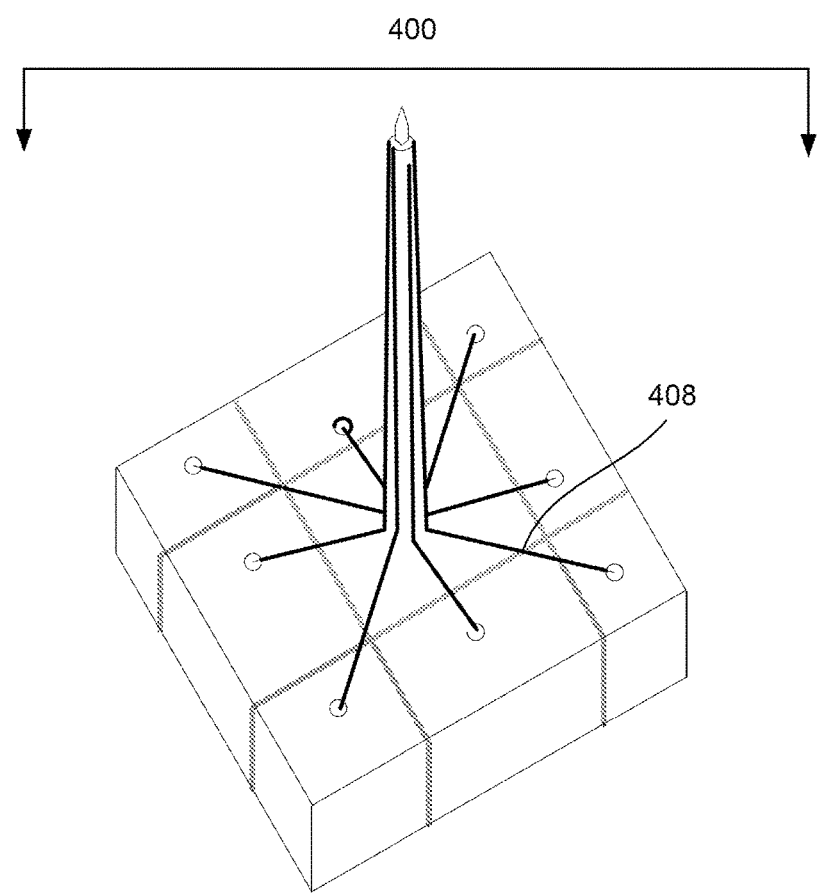
FIG. 4 is a metal layer patterned on an individual microneedle of a corresponding high aspect ratio microneedle array.

When a high aspect ratio shadow mask is placed over an array, the plurality of openings 306 on each of the individual hollow high aspect ratio projections 304 (as shown in FIG. 3) can allow for a metal layer 408 to be patterned on the individual microneedles 400 of a corresponding high aspect ratio microneedle array as illustrated in FIG. 4. The metal layer that is formed, can thereby be used in combination with the electrodes at the tip of each microneedle to form conductive pathways that also serve as electrodes along the sides of the microneedles in the array. The location of these conductive pathways along the sides of the microneedles allow for neurons along the sides of the microneedles to be stimulated by the electrodes when the array is used.

Although the conductive pathways can typically be formed of a metal, any conductive metal material may be suitable. In one example, the conductive pathways can formed of silver, copper, gold, aluminum, molybdenum, zinc, lithium, tungsten, brass, carbon, nickel, iron, palladium, platinum, tin, bronze, carbon steel, lead, titanium, stainless steel, mercury, chromium, conductive polymers, composites thereof, alloys thereof, and combinations thereof. In one example, the conductive pathways can be a metal layer which is formed of chromium and nickel. In one example, the conductive pathways can be a straight line.

Turning now specifically to, the high aspect ratio shadow mask, the high aspect ratio shadow mask can be composed of any material having enough strength to be mechanically stable for the intended use. In some embodiments the material can comprise nickel, platinum, gold, parylene, polyimide, polydimethylsiloxane, polytetrafluoroethylene (TEFLON), silicon, silicon nitride, silicone oxide, acrylic, or a combination thereof. In one example, the high aspect ratio shadow mask can comprise acrylic, polytetrafluoroethylene, poly dimethyl siloxane, or a combination thereof. In another example, the high aspect ratio shadow mask can be formed of silicon. In yet another example the, the high ratio shadow mask can be formed of nickel. In a further example, the high ratio shadow mask can be formed of poly dimethyl siloxane. In one embodiment, the base layer and plurality of hollow high aspect ratio projections can be composed of the same materials. In other embodiments, the base layer and plurality of hollow high aspect ratio projections can be composed of different materials.

In some embodiments the high aspect ratio shadow mask can be comprised of a material that allows the high aspect ratio shadow mask to be used on multiple occasions. Materials that allow for multiple reuse include materials that exhibit significant strength and allow for release from a microelectrode array. For example, a reusable high aspect ratio shadow mask can comprise nickel, platinum, gold, titanium, alloys thereof, or a combination thereof. In some examples, the releasable shadow mask can be used in combination with one or more of a lubricant and a sacrificial layer that assists in the release of the high aspect ratio shadow mask from the microelectrode array.

In other embodiments, the high aspect ratio shadow mask can comprise a dissolvable material. Non-limiting exemplary dissolvable materials can include photoresist, polyethylene glycol (PEG), or a combination thereof. For example, the dissolvable material can dissolve upon exposure to acids, certain wavelengths of light, or the like. In one example, the material can dissolve upon exposure to ultraviolet light within a 20 second period of time or contact with developer chemicals within a 2 minute period of time. In another example, the material can dissolve upon exposure to ultraviolet light or developer chemicals within a 1 minute to a 3 minute period of time. In yet a further example, the material can dissolve upon exposure to ultraviolet light or developer chemicals in less than 5 minutes. In some other examples, the materials can take larger periods of time to dissolve upon exposure to ultraviolet light or developer chemicals. For example, the materials can generally dissolve within about 1 hour, and typically within 24 hours.

With respect to the structure of the high aspect ratio shadow mask the substantially planar base and hollow high aspect ratio projections can be an integrally formed as a single piece or the hollow high aspect ratio projections can be coupled to the substantially planar base. The substantially planar base can be rigid, flexible, or semi-flexible (anything in-between rigid and flexible).

The plurality of hollow high aspect ratio projections can be arranged in a pattern on the substantially planar base layer. In some embodiments, the hollow high aspect ratio projections can be arranged as straight line rows. For example the straight line rows can comprise a 4×4 array, a 5×5 array, a 6×6 array, an 8×8 array, a 1×10 array, a 12×12 array, etc. In other embodiments, the hollow high aspect ratio projections can be in staggered rows. In another embodiment, the hollow high aspect ratio projections can be staggered based on a degree of separation from a centrally located hollow high aspect ratio projection or a designated reference location on the substantially planar base layer. The degree of separation can range anywhere from 0° to 360°. In some embodiments the degree of separation can be 30°, 45°, 60°, 75°, 90°, 120°, 150°, or 180°. In other embodiments the hollow high aspect ratio projections can be concentrically arranged in shapes such as triangles, squares, circles, or polygons. The specific arrangement of the high aspect ratio projections on the shadow mask can vary based on the desired use for the microelectrode array and the configuration of the microneedles on the array.

The shadow mask can also have a thickness which is sufficient to provide structural integrity during use, while also minimizing artifacts during deposition and/or etching of material through the plurality of openings. Thus, thickness can depend somewhat on the specific materials chosen, however as a general guideline mask thicknesses can be uniform across the mask. Similarly, mask thickness can often range from about 5 to about 100 µm, and in most cases from 10 to 25 µm.

The shape of each of hollow high aspect ratio projections can also vary. In one embodiment each of the projections in the plurality of hollow high aspect ratio projections can comprise a wide base portion that tapers to a narrow end portion. In some embodiments each of the hollow high aspect ratio projections are cone shaped. In other embodiments, each of hollow high aspect ratio projections are a triangular based pyramid shape, square based pyramid shaped, or rectangular based pyramid shape. In yet another embodiment, each of the hollow high aspect ratio projections can be extended projections having a rectangular or square cross-section (e.g. FIGS. 21-23). In a further embodiment, each of hollow high aspect ratio projections can have a polygonal shaped base that is cone shaped along the shaft, tapering to a tip section. In some other embodiments the shape of each of the hollow high aspect ratio projections can comprise a wide step like base followed by any of the projection shapes previously mentioned.

The plurality of openings on the hollow high aspect ratio projections can also vary. In one embodiment, the plurality of openings can be single opening per each hollow high aspect ratio projection. In another embodiment, the plurality of openings can comprise at least two openings on each of the high aspect ratio projections. In another embodiment, the plurality of openings can comprise three openings on each of the high aspect ratio projections. In yet another embodiment, the plurality of openings can comprise four openings on each of the high aspect ratio projections. In yet one other embodiment, the plurality of openings can comprise eight openings or more on each of the high aspect ratio projections.

Figure 5:
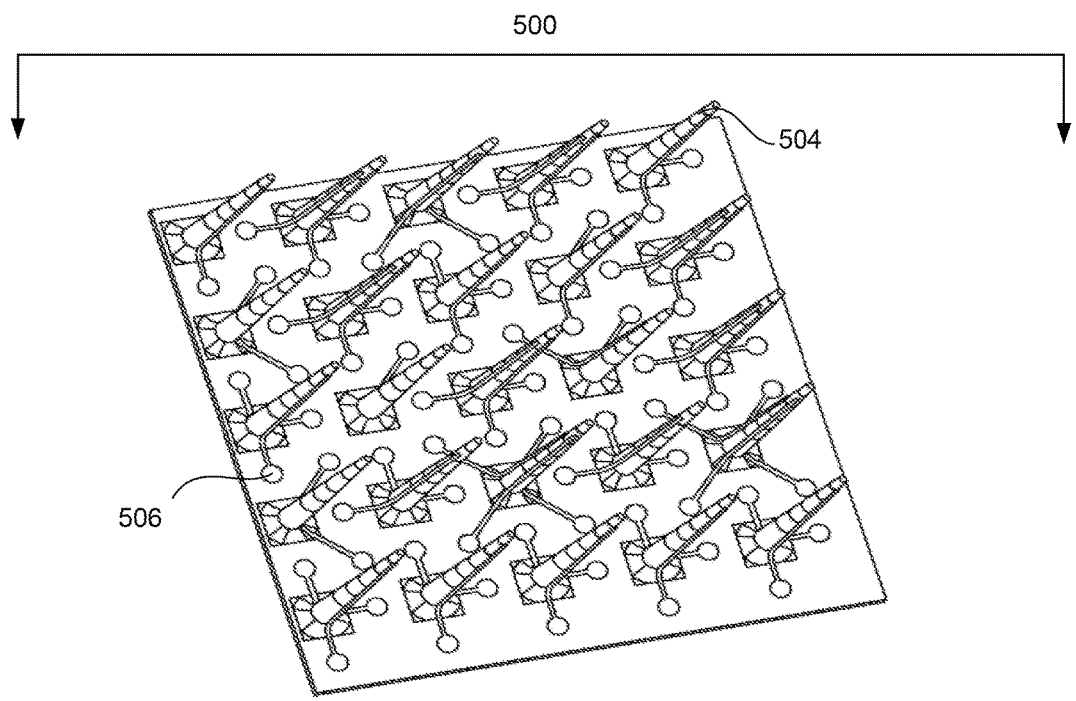
FIG. 5 is a high aspect ratio shadow mask showing a plurality of openings in accordance with one example herein.
Figure 6:
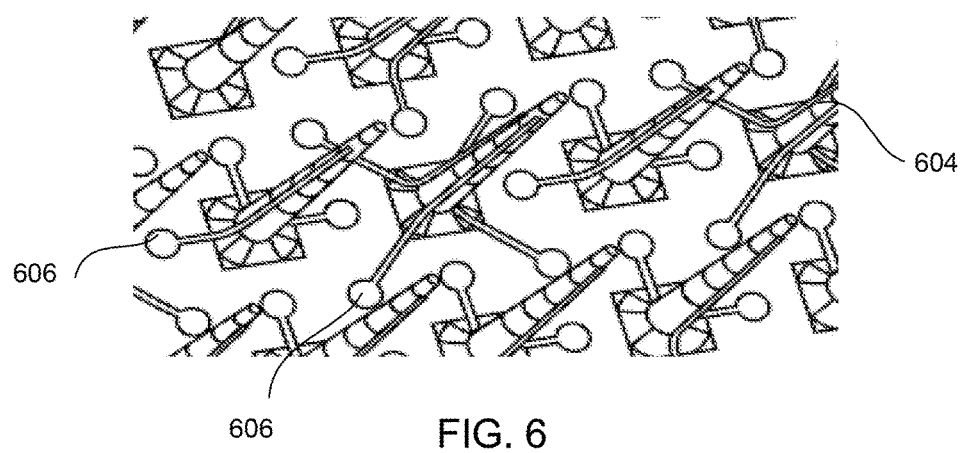
FIG. 6 is a close-up view of a portion of the high aspect ratio shadow mask as shown in FIG. 5.

In further embodiments, the plurality of openings 506 on each of high aspect ratio projections 504 on the high aspect ratio shadow mask 500 can vary between each of the high aspect ratio projections, as shown in FIG. 5. For example, one hollow high aspect ratio projection can have four openings while other hollow high aspect ratio projections can have two or three openings. In some embodiments, the variety of openings can vary based on location. As shown in FIG. 6, for example an alternating pattern can occur where some of the projections can have three openings 606 and other projections can have four openings 606 on the high aspect ratio projections 604 of the high aspect ratio shadow mask.

Figure 7:
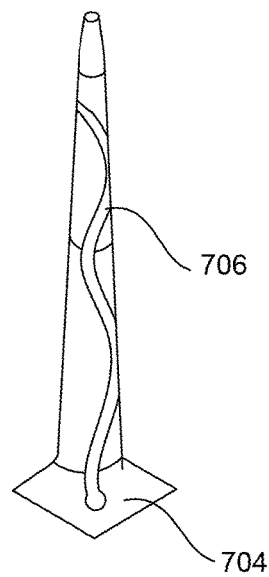
FIG. 7 is a close up view of one hollow high aspect ratio projection in a high aspect ratio shadow mask showing one of the plurality of openings as a wavy line in accordance with one example herein.
Figure 8:
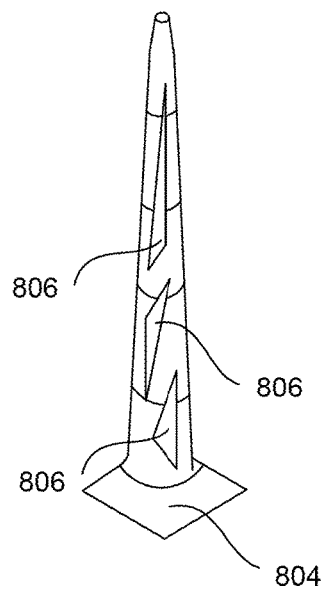
FIG. 8 is a close up view of one hollow high aspect ratio projection in a high aspect ratio shadow mask showing a plurality of openings in triangular shapes in accordance with one example herein.
Figure 9:
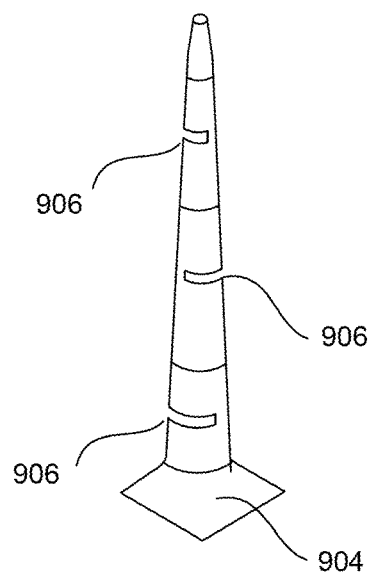
FIG. 9 is a close up view of one hollow high aspect ratio projection in a high aspect ratio shadow mask showing a plurality of openings as semi-circular open rings in accordance with one example herein.

Furthermore, the shape of the openings can also vary. For example, the openings can be slits corresponding to conductive trace pathways (e.g. narrow width and extended length). Certainly, such pathways dimensions can vary based on the size of corresponding projections. As a general guideline, conductive pathways can range from about 1 to about 100 μm and most often from 1 to 10 μm in width. However, the plurality of openings can also be provided in a wide variety of shapes. For example, the plurality of openings can be formed as wavy lines 706 dispersed along the hollow high aspect ratio projections 704, as shown in FIG. 7. In another example, the conductive pads (circular, square, triangular, rectangular, etc.) 806 at the end of traces can be dispersed along the hollow aspect ratio projections 804, as shown in FIG. 8. In yet another example, the openings can correspond to concentric circles or longitudinally transverse semi-circular rings 906, that are not fully closed and are dispersed along the hollow aspect ratio projections 904, as shown in FIG. 9. The plurality of openings can be any suitable shape and can be in any patterns to create the desired location for the formation of conductive pathways/electrodes and ultimately the desired electrode performance. In some embodiments, customized openings can be designed and used to create customized electrode patterns which can be created to target various tissue depths, spacing, tissue regions, etc.

The location of plurality of openings that form the trace deposition pattern can also vary. In some embodiments, the plurality of openings can extend from the substantially planar base layer into at least a portion of a shaft of the hollow high aspect ratio projections. In another embodiment, the plurality of openings can extend solely in a portion of a shaft of the hollow high aspect ratio projections. In further embodiments, the plurality of openings can extend along the entire portion of a shaft of the hollow high aspect ratio projections. In yet another embodiment, the location of the plurality of openings can include a combination of locations. For example, some of the openings can extend from the substantially planar base layer into at least a portion of the shaft, while other openings can be only in the shaft portion of the hollow high aspect ratio projections (e.g. to deposit on pre-existing conductive traces). Thus, in some examples, more complex patterns can be formed by sequentially utilizing different masks having differing patterns in which conductive trace pathways overlap or join to form composite conductive patterns. For example, not only complex patterns can be formed, but insulation layers can be oriented between portions of conductive pathways to form junctions (e.g. electronic device features) or non-intersecting pathways. In some examples, the location of the openings can also vary between several of the high aspect ratio projections on the high aspect ratio shadow mask. In one example, the plurality of openings that form the trace deposition pattern in each of the plurality of hollow high aspect ratio projections can vary in starting and ending point. In some embodiments, the location of the plurality of openings on each of the hollow high aspect ratio projections can vary along the circumference of the hollow high aspect ratio projections.

In some embodiments, the high aspect ratio shadow mask can further comprise a release layer oriented along an underside of the substantially planar base layer and optionally within the plurality of hollow high aspect ratio projections. The release layer can comprises polyvinyl alcohol, silicone, polymethyl methacrylate, polymethyl glutarimide, parylene, PDMS, or a photo resist material. In one example, the release layer can be polyvinyl alcohol. In one example, the polyvinyl alcohol can be spin coated.

Figure 10:
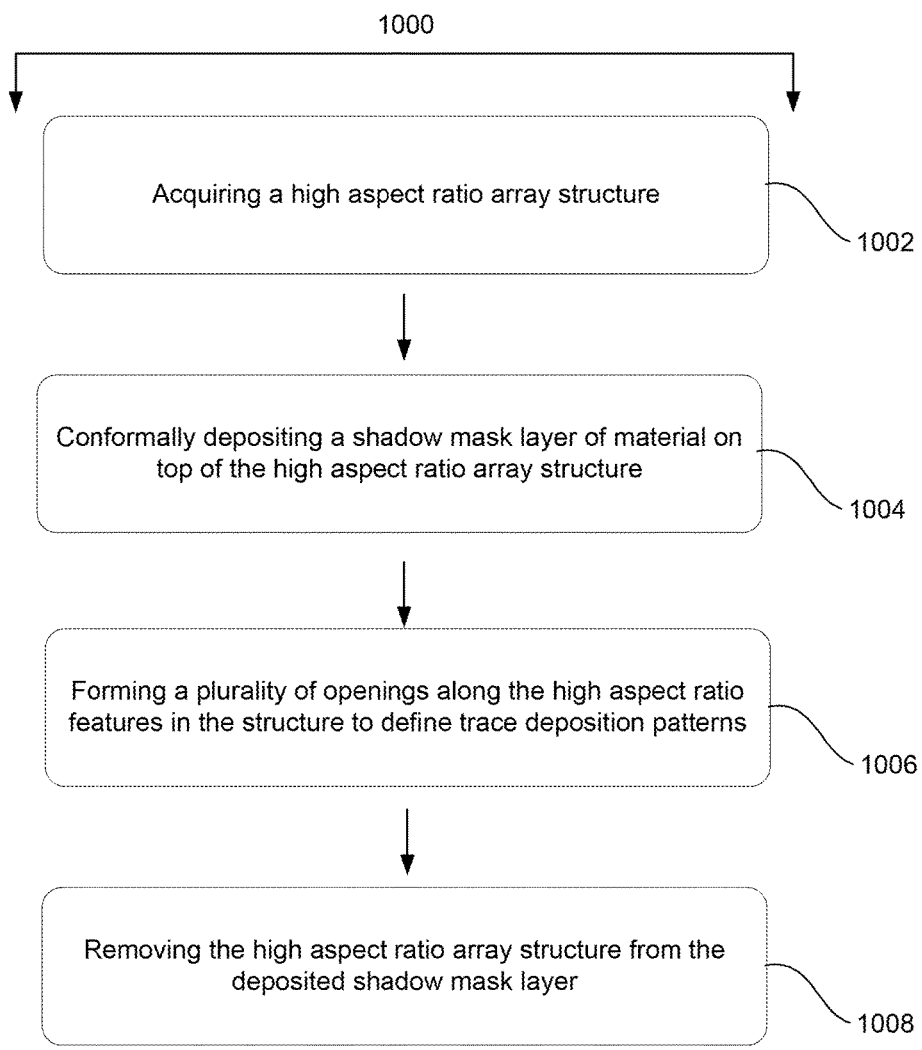
FIG. 10 is a method of making a high aspect ratio shadow mask in accordance with one example herein.

Also presented herein is a method of making a high aspect ratio shadow mask. In one embodiment the method comprises a direct deposition process, 1000. The direct deposition process, as shown in FIG. 10 can comprise (1) acquiring a high aspect ratio array structure 1002, (2) conformally depositing a shadow mask layer of material on top of the high aspect ratio array structure 1004, (3) forming a plurality of openings along the high aspect ratio features within the structure to define trace deposition patterns 1006, and (4) removing the high aspect ratio array structure from the deposited shadow mask layer 1008. In one example, the high aspect ratio structure can be a microelectrode array and can comprise electrodes. The shadow mask layer can be any of the materials described above. In some embodiments, the material of shadow mask layer can be different from the material on the uppermost surface of the high aspect ratio structure. In one example, plurality of openings can be formed using methods such as laser ablation or focused ion beam etching or plasma etching, deep reactive ion etching. In some examples, the step of removing the high aspect ratio array structure can include dissolving or detaching the high aspect ratio structure from the high aspect ratio shadow mask.

When the high aspect ratio array structure is removed by being dissolved, the high aspect ratio array structure material and the corresponding dissolving solution must be chosen so that the dissolving solution will attack the high aspect ratio array structure and not the shadow mask layer. For example, the high aspect array structure can be composed of silicon and a potassium hydroxide dissolving solution can be used to dissolve the silicon high aspect ratio array structure. After dissolving high array structure, the high aspect ratio shadow mask that is formed via the deposited shadow mask layer can be rinsed with water and used.

When the high aspect ratio array structure is removed by detaching the high aspect ratio array structure from the shadow mask layer a sacrificial release layer can be applied to assist in the removal. The sacrificial release layer can be directly applied the high aspect ratio array structure prior to depositing the layer of the shadow mask material on top of the high aspect ratio array structure. The release layer can be deposited using a photo resist or other releasable material. Non-limiting examples of suitable releasable materials used to create the sacrificial release layer can include polyvinyl alcohol, silicone, polymethyl methacrylate, polymethyl glutarimide, parylene, PDMS, or a photo resist. In one example, the sacrificial release layer can be polyvinyl alcohol. In another example, the sacrificial release layer can be photo resist.

Following the formation of the plurality of openings a chemical solution can be applied to dissolve the release layer. The chemical solution and the release layer material can be chosen so that the chemical solution will attack the release layer and not the high aspect ratio array structure or the shadow mask layer. Non-limiting exemplary chemical solutions can include acetone, water, acids, and the like. The chemical solution used to dissolve the sacrificial release layer can vary based on the material of the sacrificial release layer. For example, in the case of a photoresist material used as a sacrificial release layer, the chemical solution can be a developer or acetone. In one example, when the sacrificial release layer is silicon the chemical solution can be potassium hydroxide. In some embodiments, the chemical solution can be applied in a sonication bath or while stirring to help dissolve the release layer.

In some embodiments, an electroplating approach can be used to create the high aspect ratio shadow mask. In this method the step of depositing the shadow mask layer of material is a deposited seed layer. In one embodiment, the seed layer can range from about 50 nm to about 100 nm in thickness. In another embodiment, the seed layer can range from about 25 nm to about 75 nm. In yet another embodiment, the seed layer can range from about 10 nm to about 45 nm. In a further embodiment, the seed layer can range from about 100 nm to about 150 nm in thickness.

The plurality of openings are then formed as previously discussed. Electroplating can occur after patterning the plurality of openings on the shadow mask layer. This can allow for a thicker shadow mask to be formed while reducing the complexity involved in forming the plurality of openings in a thicker material. In some embodiments, laser or focused ion beam etching can be conducted while the materials are in the electroplating solution. In this embodiment, the laser or focused beam etching should not react with the electroplating solution.

The electroplating process can use any electric current that will not destroy the high aspect ratio array structure but will allow for the seed layer to form a coherent coating on the high aspect ratio array structure. The current required will vary based on the material of the high aspect ratio array structure and the seed layer. However, in some examples, the current can range from about 1 to about 50 mA/cm$^2$.

In some examples, a release layer can be used during the electroplating process. If the a release layer is used, then the release material can be chosen such that the release layer will withstand the deposition temperature, the deposition current, and the pressure of the seed layer. Exemplary release layer materials that can be used with an electroplating approach can include, but are not limited to, nickel, gold, titanium, platinum, zinc, copper, and the like.

In one embodiment, the step of depositing the shadow mask layer comprises plasma enhanced chemical vapor deposition. During this process the material used to form the high aspect ratio shadow mask can be deposited in a gas state to the high aspect array structure. Exemplary materials that can be used to create the high aspect ratio shadow mask using a plasma enhanced chemical vapor deposition process can include silicon, silicon nitride, silicon dioxide, parylene, or a combination thereof.

In yet another embodiment, the method of making the high aspect ratio shadow mask can comprise a negative mold approach. The negative mold approach can be used in conjunction with any of the methods above to create the high aspect ratio shadow mask. However, the high aspect ratio array structure that is used is a mold created from a high ratio aspect shadow mask. When the negative mold approach is utilized, the mold can be comprised of acrylic, TEFLON, polydimethylsiloxane, or another polymeric substance. In one example, the mold can be created by coating the material on a high aspect ratio array and then curing the material. The array can then be dissolved (e.g. in acid) resulting in a hollow mold. The mold can then be used as the high aspect ratio array structure in any of the above methods.

In further embodiment, a method of making a high aspect ratio shadow mask can involve 3D printing. In this method, the shadow mask can be graphically drawn in a computer program and printed using a 3D printer. The graphics program can be any graphics program that allows for 3D drawing. Exemplary programs include AutoCad®, Microsoft® Vizio, and Poser®. The three dimensional printer can be any 3D printer capable of printing microstructures.

Further presented herein is a method of using a high aspect ratio shadow mask to create an electrode pattern on a high aspect ratio microelectrode array. The method can comprise (1) acquiring a high aspect ratio shadow mask, (2) acquiring a high aspect ratio array structure, (3) aligning the high aspect ratio shadow mask over the high aspect ratio array structure, (4) depositing trace deposition materials over the high aspect ratio shadow mask, wherein the deposited trace deposition materials penetrate through the plurality of openings along the hollow projections to form an electrode pattern on the high aspect ratio array structure, and (5) removing the high aspect ratio shadow mask to yield the microelectrode array structure comprising the electrode pattern. The high aspect ratio shadow mask can be as described above. The step of aligning the high aspect ratio shadow mask over the high aspect ratio array structure can occur during formation of the mask or via placement of a mold that was previously created. In some embodiments, the trace deposition materials comprise a negative photoresist material and the method further comprises applying UV light before removing the high aspect ratio shadow mask from the microelectrode array structure.

EXAMPLES

Example 1—Direct Deposition

A high aspect ratio shadow mask was created using the direct deposition method. First, a Utah electrode array (UEA) having a 5×5 configuration with a 800 μm pitch and 1.5 mm long high aspect ratio projections was used as a base layer. The UEA was comprised of silicon. Then a 5 µm thick silicon nitride layer was deposited on top of the UEA using plasma enhanced chemical vapor deposition (PECVD) to form the high aspect ratio shadow mask. The PECVD process was carried out in an Oxford 80 PECVD at 300° C. and gases used were silane and nitrogen. The UEA with the high aspect ratio shadow mask was then placed in a potassium hydroxide solution at 90° C. for approximately 20 hours. The UEA was dissolved leaving a portion of the high aspect ratio shadow mask behind. Reducing the contact time with the potassium hydroxide solution in the future may result in a more complete structure being left behind.

Example 2—Use of a Release Layer

A high aspect ratio shadow mask was created using a sacrificial release layer. First, a Utah electrode array (UEA) having a 5×5 configuration with a 800 µm pitch and 1.5 mm long high aspect ratio projections was used as a base layer. The UEA was comprised of silicon. Then a sacrificial release layer comprised of two spin coated photo resist (AZ9260) layers was applied over the UEA. Following this, a PDMS layer was spin coated on top of the photo resist layer to form the high aspect ratio shadow mask. The device was then cured. Following curing, acetone was used to dissolve the photoresist release layer and the UEA was detached leaving behind a high aspect ratio shadow mask formed from the PDMS layer. The PDMS was very thin along the hollow high aspect ratio projections and collapsed. In the future, we believe that the structure can be improved by applying multiple PDMS layers to achieve the desired thickness.

Example 3—Electroplating & Use of the Resulting Shadow Mask

A high aspect ratio shadow mask was created using electroplating. First, a Utah electrode array (UEA) having a 5×5 configuration with a 800 µm pitch and 1.5 mm long high aspect ratio projections was used as a base layer. The UEA was comprised of silicon. Then a 1 µm thick silicon nitride layer was deposited over the UEA using plasma enhanced chemical vapor deposition (PECVD). A laser was then used to create holes through silicon nitride layer and expose the silicon underneath. These openings were used as a path for current during electroplating. Following this a seed layer was deposited on to the coated UEA. The seed layer consisted of 100 µm Cr and 160 µm Ni. Following application of the seed layer a laser was used to create patterns in the seed layer. The device was then placed in an electroplating solution with Ni salt and a Ni anode for 3 hours with 10 mA of current. A potassium hydroxide (PSE-200) solution was applied at 90° C. to dissolve the underlying structure. It took nearly 19 hours to completely dissolve the silicon structure. The high aspect ratio shadow mask was collected and rinsed with water.

Example 4—Use of a Shadow Mask to Deposit Metal on a UEA

The shadow mask created in Example 3 was used to deposit metal through the plurality of openings on the microneedles of an UEA. First, a UEA device was placed within the shadow mask. Metal was then deposited over the shadow mask. The metal penetrated through the plurality of openings and adhered to microneedles on the UEA.

Example 5—Electroplating & Use of the Resulting Shadow Mask

A high aspect ratio shadow mask was created using electroplating. First, a Utah electrode array (UEA) having a 5×5 configuration with a 800 µm pitch and 1.5 mm long high aspect ratio projections was used as a base layer. The UEA was comprised of silicon. Then a 1 µm thick silicon nitride layer was deposited over the UEA using plasma enhanced chemical vapor deposition (PECVD). A laser was then used to create holes through silicon nitride layer and expose the silicon underneath. These openings were used as a path for current during electroplating. Following this a seed layer was deposited on to the coated UEA. The seed layer consisted of 100 µm Cr and 160 µm Ni. Following application of the seed layer a laser was used to create patterns in the seed layer. The device was then placed in an electroplating solution with Ni salt and a Ni anode for 3 hours with 10 mA of current. A potassium hydroxide (PSE-200) solution was applied at 90° C. to dissolve the underlying structure. It took nearly 19 hours to completely dissolve the silicon structure. The high aspect ratio shadow mask was collected and rinsed with water.

Example 6—Use of a Shadow Mask to Deposit Metal on a UEA

The shadow mask created in Example 5 was used to deposit metal through the plurality of openings onto the microneedles of an UEA. First, the shadow mask was placed on a second 5×5 UEA. A laser ion beam was used to open up the patterns. This shadow mask now comprised a plurality of openings along the hollow projections. Metal (40 nm TiW and 500 nm Pt) was deposited over the shadow mask. The metal penetrated the plurality of openings and adhered to the UEA.

Example 7—Negative Mold

A Utah electrode array (UEA) having a 5×5 configuration with a 800 µm pitch and 1.5 mm long high aspect ratio projections was used as a base layer. We then spun coat polyvinyl alcohol (PVA) three times on top of UEA. The device was placed in a small sample preparation cup and acrylic was poured into the cup. The cup, acrylic, and device were placed in a high-pressure chamber for 2 hours and 40 psi. After curing, the device with acrylic was removed from the sample preparation cup and placed in water. After a couple of hours, the PVA layer dissolved and the UEA was separated from acrylic forming an acrylic mold. The acrylic mold was polished in order to open up the needle tips. A metal seed layer (40 nm Chromium and 100 nm Nickel) was deposited inside the mold and electroplated in a nickel solution. The acrylic mold was dissolved in acetone leaving behind the nickel shadow mask.

Example 5—3D Printing

AutoCad® was used to draw a three dimensional shadow mask. The shadow mask structure was then printed using a 3D printer (3D Laser Nanolithography System, Nanoscribe GmbH, Germany).

The foregoing detailed description describes the invention with reference to specific exemplary embodiments. However, it will be appreciated that various modifications and changes can be made without departing from the scope of the present invention as set forth in the appended claims. The detailed description, examples, and accompanying drawings are to be regarded as merely illustrative, rather than as restrictive. It is therefore intended that the invention be limited only by the scope of the appended claims.

What is claimed:

1. A high aspect ratio shadow mask, comprising:
a substantially planar base layer, and
a plurality of hollow high aspect ratio projections extending from the substantially planar base layer, wherein said hollow high aspect ratio projections have an aspect ratio of at least 8:1 and further comprising a plurality of openings along the hollow high aspect ratio projections defining trace deposition patterns.

2. The high aspect ratio shadow mask of claim 1, wherein shadow mask comprises a member selected from the group consisting of nickel, platinum, gold, parylene, polyimide, poly dimethyl siloxane, polytetrafluoroethylene, silicon, silicon nitride, silicone oxide, acrylic, or a combination thereof.

3. The high aspect ratio shadow mask of claim 1, wherein the high aspect ratio shadow mask comprises a dissolvable material that dissolves upon exposure to ultraviolet light within 20 seconds or upon contact with a developer within 2 minutes.

4. The high aspect ratio shadow mask of claim 1, wherein the substantially planar base layer is flexible.

5. The high aspect ratio shadow mask of claim 1, wherein the substantially planar base layer and the hollow high aspect ratio projections comprise a single integrally formed structure.

6. The high aspect ratio shadow mask of claim 1, wherein the plurality of hollow high aspect ratio projections are arranged in a pattern on the substantially planar base layer.

7. The high aspect ratio shadow mask of claim 1, wherein the plurality of hollow high aspect ratio projections each comprises a wide base portion that tapers to a narrow end portion.

8. The high aspect ratio shadow mask of claim 7, wherein the plurality of hollow high aspect ratio projections are each cone shaped.

9. The high aspect ratio shadow mask of claim 7, wherein the plurality of hollow high aspect ratio projections are either a triangular based pyramid shape or a square based pyramid shape.

10. The high aspect ratio shadow mask of claim 1, wherein the plurality of hollow high aspect ratio projections extend substantially perpendicular from the planar base layer.

11. The high aspect ratio shadow mask of claim 1, wherein the trace deposition patterns include at least two traces on each of the high aspect ratio projections.

12. The high aspect ratio shadow mask of claim 1, wherein the plurality of openings extend from the substantially planar base layer into at least a portion of a shaft of the hollow high aspect ratio projections.

13. The high aspect ratio shadow mask of claim 1, wherein the high aspect ratio shadow mask further comprises a release layer oriented along an underside of the substantially planar base layer and optionally within the plurality of hollow high aspect ratio projections.

14. The high aspect ratio shadow mask of claim 13, wherein the release layer comprises polyvinyl alcohol, silicone, polymethyl methacrylate, polymethyl glutarimide, or a photo resist material.

15. A method of making a high aspect ratio shadow mask, comprising
acquiring a high aspect ratio array structure;
conformally depositing a shadow mask layer of material on top of the high aspect ratio array structure, wherein a plurality of openings are formed along high aspect ratio features within the structure to define trace deposition patterns, wherein said high aspect ratio features have an aspect ratio of at least 8:1; and
removing the high aspect ratio array structure from the deposited shadow mask layer.

16. The method of claim 15, wherein the high aspect ratio array structure further comprises electrodes.

17. The method of claim 15, wherein the method further comprises a step of drying the deposited shadow mask layer prior to dissolving or detaching the high aspect ratio array structure.

18. The method of claim 15, wherein the method further comprises applying a release layer to the high aspect ratio array structure prior to depositing the shadow mask layer of material on top of the high aspect ratio array structure.

19. The method of claim 15, wherein the deposited shadow mask layer is a seed layer and the method further comprises electroplating the high aspect ratio shadow mask after patterning the plurality of openings on the shadow mask layer.

20. The method of claim 15, wherein the step of depositing the shadow mask layer comprises plasma enhanced chemical vapor deposition.

21. A method of using a high aspect ratio shadow mask to create an electrode pattern on a high aspect ratio microelectrode array, comprising
acquiring a high aspect ratio shadow mask comprising;
a substantially planar base layer;
a plurality of hollow high aspect ratio projections extending from the substantially planar base layer, wherein said hollow high aspect ratio projections have an aspect ratio of at least 8:1; and
a plurality of openings along the hollow high aspect ratio projections defining trace deposition patterns;
acquiring a high aspect ratio array structure;
aligning the high aspect ratio shadow mask over the high aspect ratio array structure;
depositing trace deposition materials over the high aspect ratio shadow mask, wherein the deposited trace deposition materials penetrate through the plurality of openings along the hollow projections to form an electrode pattern on the high aspect ratio array structure; and
removing the high aspect ratio shadow mask to yield the microelectrode array structure comprising the electrode pattern.

22. The method of claim 21, wherein the trace deposition materials comprise a negative photoresist material and the method further comprises applying UV light before removing the high aspect ratio shadow mask from the microelectrode array structure.

* * * * *